United States Patent [19]
Perry

[11] Patent Number: 5,942,500
[45] Date of Patent: Aug. 24, 1999

[54] DIETARY COMPOSITION TO REDUCE DIETARY FATS

[76] Inventor: Stephen C. Perry, 205 Churchill Dr., Longwood, Fla. 32779

[21] Appl. No.: 09/067,532

[22] Filed: Apr. 27, 1998

[51] Int. Cl.$^6$ .................................................. A01N 43/04
[52] U.S. Cl. ................................ 514/55; 435/198; 514/2; 514/54; 536/20
[58] Field of Search .............................. 435/198; 514/54, 514/2, 55; 536/20

[56] References Cited

U.S. PATENT DOCUMENTS

| 5,434,141 | 7/1995 | Schafer | 514/53 |
| 5,453,282 | 9/1995 | Kanauchi | 424/464 |
| 5,681,819 | 10/1997 | Tang | 514/12 |

OTHER PUBLICATIONS

Olivecrona, Canadian J. Cardiol. 73G–78G, Oct. 1995.
Bensadoun, Ann. Rev. Nutrition 11, 217–237, 1991.

*Primary Examiner*—Cecilia J. Tsang
*Assistant Examiner*—David Lukton
*Attorney, Agent, or Firm*—Malin, Haley, DiMaggio & Crosby, PA

[57] ABSTRACT

A method and composition for reducing dietary fats while consuming a meal containing substantial portions of dietary fats, for reducing and inhibiting LDLs and triglyceride levels in the bloodstream by consuming the composition comprising a linear aminopolysaccharide of the structure similar to and including (1–4)—linked 2-amino-2-deoxy-Beta-D-gluco pyranose, lipoprotein lipase, calcium poly ascorbate and propanetricarboxylic acid. Preferably, the linear aminopolysaccharide of the structure similar to and including (1–4)—linked 2-amino-2-deoxy-Beta-D-gluco pyranose is made from fungal or yeast or other plant source. The lipoprotein lipase enhances the process and the acid acts as an appetite suppressant. If the composition is taken approximately 15 minutes before a meal containing significant amounts of dietary fat, the present invention will reduce weight, reduce bad cholesterol and triglycerides in the bloodstream, and increase HDLs, while suppressing appetite.

10 Claims, No Drawings

DIETARY COMPOSITION TO REDUCE DIETARY FATS

BACKGROUND OF THE INVENTION

1. Field of the Invention

This invention relates to a composition providing a dietary supplement to inhibit the digestion of low-density lipoproteins (LDLs) thereby reducing the amount of cholesterol present in the bloodstream while consuming a food containing lipids, to reduce weight, and to increase high-density lipoproteins (HDLs) for improved human health.

2. Description of Related Art

Fats, also called lipids, are energy-rich substances that serve as major sources of fuel for the body's metabolic processes. Fats are obtained from food (meats, oils, and the like) and are formed in the body, mostly in the liver, and can be stored in fat cells for future use. Fat cells also insulate the body from cold and help protect the body from injury. Fats are essential components of cell membranes of the myelin sheaths that surround nerve cells and of bile.

The two major fats in the blood are cholesterol and triglyceride. The fats attach themselves to certain proteins so they can travel throughout the bloodstream; the combined fats and proteins are called lipoproteins, which are discussed below.

The body regulates lipoprotein levels in several ways. One way is by reducing the synthesis of lipoproteins and their entry into the bloodstream. Another is by increasing or decreasing the rate at which lipoproteins are removed from the blood.

Heart disease is the number one fatal disease in the United States. More than one million people suffer from heart attacks annually, and more than half of those people die.

The most common form of heart disease is arteriosclerosis or "hardening of the arteries." Arteriosclerosis is a progressive disease in which the interior walls of an artery become coated with fatty substances, such as cholesterol.

Arteriosclerosis develops slowly over the years. Fat and cholesterol, mixed with smooth muscle cells and calcium, form a material called plaque that builds up on the inside of artery walls.

The rate at which plaque builds up on the walls of arteries is dependent upon how much cholesterol the arteries are exposed to. Cholesterol is a waxy substance generated primarily in the liver. It is also found in foods of animal origin, such as meats and dairy products.

Cholesterol is a part of all cell membranes and is needed to make sex hormones, vitamin D, and bile, which allows humans to digest fats. Although cholesterol is important to the body, large amounts of cholesterol are not really needed in the diet because the liver makes a sufficient amount. Some scientific knowledge suggests that the way cholesterol is transported through the blood is even more significant in the development of arteriosclerosis. Cholesterol does not travel through the blood freely by itself, but is wrapped in a protein package.

A tiny glob of fat wrapped in protein is called a lipoprotein.

There are different types of lipoproteins which also differ in the amount of cholesterol and other fats they carry and are identified by their densities. Low-density lipoproteins are referred to as LDLs, and are sometimes referred to as "bad cholesterol." High-density lipoproteins are referred to as HDLs, and are considered "good cholesterol." There are also very low- density lipoproteins, VLDLs, which eventually get converted to LDLs.

LDLs are the main carriers of cholesterol and contain less protein and more lipids, or fats, than HDLs. As the LDLs travel through the arteries, carrying cholesterol to cells, LDLs can interact with existing plaque buildup, shedding the protein barriers, causing cholesterol to be deposited along artery walls, which adds to the accumulation of plaque.

On the other hand, HDLs can actually help remove cholesterol Adfrom the body because HDLs pick up excess cholesterol which is carried back to the liver, and is eventually excreted.

Serum cholesterol (blood cholesterol) is measured by a blood test that determines milligrams of cholesterol in a deciliter of blood (MG/DL).

As LDLs travel through the bloodstream, they are attracted and pulled into cells by special protein receptors on the surface of the cells. Only the LDLs that are not caught by receptors are carried to the liver, where they are converted into bile acid and eventually excreted by the body. When a person consumes too much lipids or fats, such as animal fats, for a meal, the bloodstream can become flooded with tiny particles carrying fats and cholesterol, digested in the intestines, out to the rest of the body. The liver becomes overtaxed trying to get rid of fatty particles based on excess LDLs in the blood. Therefore, the excess LDL particles circulating through the bloodstream, lead to the formation of plaques. HDLs travel through the bloodstream picking up bits of excess cholesterol and carrying them back to the liver for processing. In addition to studies regarding LDLs in the blood and HDLs in the blood, much research has centered around the consumption of animal fats in the human diet.

Triglycerides are made up of three fatty-acid molecules attached to one molecule of glycerol. These fatty acids can be saturated or unsaturated. Triglycerides make up approximately 95 percent of the fat and oil that human beings consume, as well as the fat traveling through the bloodstream, and which is stored in the body. Like cholesterol, a high level of triglycerides in the blood has been linked to coronary heart disease. When sugar is consumed, triglyceride levels in the blood rise. There is scientific controversy over how much of a factor sugar is in the development of coronary disease. There is a controversy as to whether or not the temporary rise in triglycerides caused by sugar consumption is dangerous for most people. The present invention also has the purpose of controlling or reducing the amount of triglycerides present in the bloodstream by preventing their absorption into the digestive process by reducing or eliminating triglycerides prior to the digestive process.

Fats that humans eat are saturated, mono-unsaturated, and polyunsaturated. Saturated fats that are generally solid at room temperature are the most likely to increase serum cholesterol. The liver uses saturated fat to make cholesterol, so that the more saturated fat a food contains, the more it is likely to raise serum cholesterol. Saturated fats are found in meats, dairy products, milk, butter, cream, and cheese, as well as some oils, such as coconut oil and palm oil, which are high in saturated fats.

Polyunsaturated fats are soft or liquid at room temperature, and encompass vegetable oils, such as corn, cottonseed, soybean, sunflower, and safflower oils. Polyunsaturated fats tend to lower the level of cholesterol in the blood.

Mono-unsaturated fats, such as olive and peanut oil, may equal or be even better than polyunsaturates at reducing levels of harmful cholesterol. The fat in cold water fish is polyunsaturated, which allows it to stay liquid in even very cold water.

Therefore, based on the most recent studies, lowering LDL cholesterol amounts and increasing HDL cholesterol during consumption of animal fats and dairy products would be more beneficial for human health.

Although changing one's diet is certainly one way to achieve these objectives, it is difficult in the United States and other Western industrialized nations' cultures to achieve a fat-free or minimal fat diet because of the foods available.

The present invention provides a way to lower the serum LDL cholesterol amounts, while allowing a person to eat meats and dairy products using natural and prepared dietary supplements that are believed to reduce or inhibit the absorption and ingestion of lipids into the cells by binding LDL cholesterol before the LDLs get into the bloodstream, allowing the LDLs to pass through a person's body without being ingested into the bloodstream. The LDLs are based on fat substances that pass through the body through normal excretion.

The use of the present invention provides for a dietary supplement made of a composition of ingredients that produce a synergistic interaction of natural ingredients that greatly reduce dangerous cholesterol and triglyceride levels to reduce the possibility of coronary disease and can act to aid in weight loss by preventing fats from being absorbed into the bloodstream or cells in the body.

Drugs have been used to lower levels of blood fats in human beings. For example, bile acid absorbers, such as cholestyramine and colestipol bind bio-acids in the intestine which enhances LDL removal from the bloodstream.

Niacin has been used to reduce the rate of VLDL production, which is the forerunner of LDL, and acts as a lipoprotein synthesis inhibitor.

Also, coenzyme A reductase inhibitors, such as fluvastatin, lovastatin, pravastatin, and simvastatin, are drugs that block the synthesis of cholesterol, enhancing the removal of LDL from the bloodstream. Finally, fibric acid derivatives, such as clofibrate, fenofibrate, and gemfibrozil, aid in the breakdown of fats.

However, the use of drugs often includes undesirable side effects.

The present invention provides for dietary supplements in a composition formed from natural elements which work together to greatly reduce and inhibit the amounts of LDLs, or bad cholesterol, and triglycerides in the body. This will result in lowering overall cholesterol amounts, and should aid in weight loss.

U.S. Pat. No. 4,223,023, issued Sep. 16, 1980 to Furda, describes a non-absorbable lipid binder that uses chitosan as a food additive or as a pharmaceutical preparation to reduce absorption of lipids. U.S. Pat. No. 5,453,282, issued Sep. 26, 1995 to Kanauchi et al., describes dietary lipid digestion/absorption inhibitory agents and ingesta. This agent is comprised of a mixture of chitosan and ascorbic acid or a salt thereof. Both of these patents are for the treatment of obesity.

The chitin of insect exoskeletons and fungal cell walls is another extraordinarily abundant organic substance and is a polysaccharide, and in fact a linear polymer of a sugar derivative called N-acetylglucosamine. Chitosan is prepared by the alkaline deacetylation of chitin with concentrated sodium hydroxide at elevated temperatures. U.S. Pat. No. 4,223,023 discusses the effect of chitosan and its capabilities of binding very fatty acids to form corresponding complex salts. The chitosan-fatty acid complex, after ingestion by a mammal, will bind additional lipids due to its strong hydrophobic characteristics, which would include natural triglycerides, fatty and bile acids, and cholesterol and other sterols, and a great portion of these bile lipids will be excreted rather than absorbed and utilized by the human.

BRIEF SUMMARY OF THE INVENTION

The present invention provides a composition made from dietary ingredients and a method to reduce LDL cholesterol levels and reduce triglycerides, while increasing HDL cholesterol in a human being during a meal containing animal meats and/or dairy products containing lipids. A secondary benefit is that it is possible that weight reduction can be obtained, even though the person consumes dietary lipid fats.

The composition in accordance with the present invention utilizes linear aminopolysaccharide of the structure similar to and including (1–4)—linked 2-amino-2-deoxy-Beta-D-gluco pyranose with a second active ingredient, lipoprotein lipase, which is an enzyme produced from plants such as wheat germ and castorbean or from fungi similar to but not necessarily "Rhizopus delemar" or other viable plant or fungi source. The addition of lipoprotein lipase works in concert with the linear aminopolysaccharide of the structure similar to and including (1–4)—linked 2-amino-2-deoxy-Beta-D-gluco pyranose actively to produce much lower blood cholesterol levels, and especially lowering LDL (bad cholesterol) levels. The composition also includes an acid that is designed to make the lipoprotein more active, the acid being calcium poly ascorbate. The calcium molecule is the metal ion required by the lipoprotein lipase as a cofactor to maximize its activity.

The composition of the present invention to reduce bad cholesterol also includes the element of a carbolic acid of 2-hydroxy-1, 2, 3-propanetricarboxylic acid. This enhances the swelling action of the linear aminopolysaccharide of the structure similar to and including (1–4)—linked 2-amino-2-deoxy-Beta-D-gluco pyranose which leads to a sense of fullness in the human being, producing appetite suppression and a fullness effect.

The dietary supplement composition in accordance with the present invention is taken prior to a meal that contains fatty acids and an appreciable amount of dietary fat. The particular composition in accordance with the present invention would not be taken before or with meals that have no fat.

The present composition could be represented by approximately 55–65 percent by weight of linear aminopolysaccharide of the structure similar to and including (1–4)—linked 2-amino-2-deoxy-Beta-D-gluco pyranose combined with approximately 15–25 percent by weight of lipoprotein lipase and calcium poly ascorbate and combined with approximately 10–20 percent of the propanetricarboxylic acid. The ingredients are blended together, compounded with available dietary ingredients, and would be taken approximately 15 minutes prior to a meal and with a meal, as long as the meal contains an appreciable amount of dietary fat.

Variations in the amounts of the compound can range for the linear aminopolysaccharide of the structure similar to and including (1–4)—linked 2-amino-2-deoxy-Beta-D-gluco pyranose, 450 to 750 parts; the lipoprotein lipase enzyme, 100 to 200 parts; calcium poly ascorbate 25–45 parts by weight and the 2-hydroxy-1, 2, 3-propanetricarboxylic acid, from 80 to 160 parts per weight.

The method of reducing or inhibiting LDL cholesterol in the human diet and also inhibiting and reducing triglycerides in the human diet involves supplementing a meal containing large amounts of dietary fat, such as animal meats and/or dairy products, with a composition that includes approximately 63 percent linear aminopolysaccharide of the structure similar to and including (1–4)—linked 2-amino-2-deoxy-Beta-D-gluco pyranose especially that made from fungi, yeast, or other plant sources, in combination with approximately 20 percent lipoprotein lipase and calcium poly ascorbate and 16 percent propanetricarboxylic acid. The method involves ingesting or taking preferably up to 2100 milligrams of the composition approximately 15 minutes prior to a meal having large amounts of dietary fat. It is believed that using this method, a human being can still continue to consume dietary fats, while at the same time reduce weight gain from dietary lipids, reduce and inhibit LDLs, reduce and inhibit triglycerides, while increasing HDLs.

It is an object of this invention to provide an improved dietary supplement compound that reduces levels of undesired LDL cholesterol that can be utilized while eating dietary fats with a meal.

It is another object of this invention to provide a dietary method and compound that utilizes natural ingredients in combination and that interact with each other to reduce undesired or bad cholesterol while consuming fatty acids in dietary meals and which reduces triglycerides, with the additional benefit of weight loss if desired.

And yet another object of this invention is to provide a dietary supplement which is a composition that inhibits ingestion of LDL cholesterol while consuming a diet high in lipids produced from meats and other fatty foods.

DETAILED DESCRIPTION OF THE INVENTION

A dietary food supplement to reduce or eliminate undesired LDL cholesterol in the diet of a mammal while the mammal is able to consume dietary lipids, including animal meats and dairy products, comprising a composition of a linear aminopolysaccharide of the structure similar to and including (1–4)—linked 2-amino-2-deoxy-Beta-D-gluco pyranose used in conjunction with lipoprotein lipase enzyme, calcium poly ascorbate and 2-hydroxy-1, 2, 3-propanetricarboxylic acid.

A linear aminopolysaccharide of the structure similar to and including (1–4)—linked 2-amino-2-deoxy-Beta-D-gluco pyranose, the lipoprotein lipase and calcium poly ascorbate, and the 2-hydroxy-1,2,3-propanetricarboxylic acid are combined in predetermined ratios and may be taken as a food additive approximately 15 minutes prior to a primary meal containing lipids and fatty acids. The composition may be used to inhibit both cholesterol, that is undesired LDLs, and triglycerides.

It is important to note that this is to be taken specifically with a diet that includes fatty acids, and is not to be used if one is consuming nonfat foods, such as vegetables and juices.

The primary purpose of the invention is to reduce or totally eliminate excessive LDLs in the bloodstream by allowing unwanted LDLs to be bound in such a way with the composition of materials herein that it passes through the body without being ingested, digested, or in any way introduced into the bloodstream or the cell structure. In fact, it is passed out through excretion and never functions to provide fatty materials to the mammal's body.

EXAMPLE 1

A composition is prepared with the following ingredients:

a linear aminopolysaccharide of the structure similar to and including (1–4)—linked 2-amino-2-deoxy-Beta-D-gluco pyranose—from 450 to 750 parts by weight;

Lipoprotein Lipase—100 to 200 parts by weight, and calcium poly ascorbate 25–45 parts by weight;

2-hydroxy-1, 2, 3-propanetricarboxylic acid—80 to 160 parts by weight.

This mixture is blended by and in itself and may be taken separately as a composition approximately 15 minutes before consuming a meal that contains dietary fatty acids and triglycerides of concern to the user. The composition described herein may also be compounded with other dietary ingredients that are taken with the same meal.

The preferred amount would be between 500 mg up to 2250 milligrams of the composition per meal, or even more which could be adjusted according to the amount of lipids, fatty acids, and triglycerides in the particular type of foods.

The composition in accordance with the present invention described herein and the method of using the composition just prior to a meal having significant amounts of dietary fats significantly inhibits or reduces the bad LDLs. The lipoprotein lipase inherently hydrolizes fats into glycerol and fatty acids. Of significance, the lipoprotein lipase selectively hydrolizes only fatty acids on the end of triglycerides. Thus, the preferred lipoprotein lipase hydrolizes triglycerides in the presence of a lipoprotein complex which, would be the meal being consumed by the human being, forming glycerol and fatty acids, which are then bound by the linear aminopolysaccharide of the structure similar to and including (1–4)—linked 2-amino-2-deoxy-Beta-D-gluco pyranose preferentially, thus inhibiting its ingestion into the bloodstream. The calcium poly ascorbate enhances the activity of the lipoprotein lipase.

Another function of the lipoprotein lipase in this composition is that the lipoprotein lipase can split fats without damaging sensitive constituents, such as vitamins or unsaturated fatty acids, which are HDLs, leaving bad or saturated fats to be bound by the linear aminopolysaccharide of the structure similar to and including (1–4)—linked 2-amino-2-deoxy-Beta-D-gluco pyranose. Therefore, it is believed that the combination of the linear aminopolysaccharide of the structure similar to and including (1–4)—linked 2-amino-2-deoxy-Beta-D-gluco pyranose in conjunction with the lipoprotein lipase synergistically acts to greatly seek out and bind LDL fats, thus preventing them from going into the bloodstream and allowing them to pass safely through the human system, thereby greatly reducing cholesterol and triglyceride levels that would have been raised due to the dietary meal containing meats and/or dairy products high in fat content.

Further, the addition of the 2-hydroxy-1, 2, 3 propanetricarboxylic acid enhances the swelling action of the linear aminopolysaccharide of the structure similar to and including (1–4)—linked 2-amino-2-deoxy-Beta-D-gluco pyranose, again creating a sense of fullness, producing appetite suppression.

Again, using the method for weight reduction and reduction of cholesterol in the blood, the composition described herein would be taken approximately 15 minutes prior to a meal containing an appreciable amount of dietary fat.

In the preferred embodiment of the invention, a yeast or fungal-derived saccharide should be used for the linear aminopolysaccharide of the structure similar to and including (1–4)—linked 2-amino-2-deoxy-Beta-D-gluco pyranose. This also results in a product that is 100 percent natural. A linear aminopolysaccharide of the structure similar to and including (1–4)—linked 2-amino-2-deoxy-Beta-D-gluco pyranose derived from shellfish may also work if properly processed to remove any allergy associated with it.

In accordance with the present invention, the fungus selected is the genus aspergillus that is used for the linear aminopolysaccharide of the structure similar to and including (1–4)—linked 2-amino-2-deoxy-Beta-D-gluco pyranose and is defined as "*aspergillus terreus*" or the like from the immediate family.

Also, when using yeast as the basic active ingredient for the linear aminopolysaccharide of the structure similar to and including (1–4)—linked 2-amino-2-deoxy-Beta-D-gluco pyranose a benefit is gained from the ingredient lovastatin, which naturally occurs in "*aspergillus terreus*", but is not found in shellfish material. Lovastatin is a known anti-hyper cholesterolemic material. This would also aid in the present method for reducing cholesterol.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A dietary supplement for reducing LDL and triglyceride levels comprising a mixture of 60% (w/w) linear aminopolysaccharide and 40% (w/w) lipoprotein lipase, wherein said linear aminopolysaccharide consists of recurring (1–4)—linked 2-amino-2-deoxy-β-D-glucopyranose units.

2. A dietary supplement for reducing LDL and triglyceride levels comprising a mixture of a linear aminopolysaccharide, lipoprotein lipase and citric acid, wherein said linear aminopolysaccharide consists of recurring (1–4)—linked 2-amino-2-deoxy-β-D-glucopyranose units.

3. The composition according to claim 2 which contains 63% (w/w) of the linear aminopolysaccharide, 21% (w/w) lipoprotein lipase and 16% (w/w) citric acid.

4. The composition of claim 2 further comprising calcium polyascorbate.

5. A method of reducing the risk of primary hyperlipodemus or hypolipodemus in a human comprising administering to said human a dietary supplement according to any of claims 1–4, wherein said dietary supplement is administered prior to consumption of high-fat food.

6. The method according to claim 5, wherein said dietary supplement is administered 15 minutes prior to consumption of the high-fat food.

7. A method of reducing LDL cholesterol levels a human comprising administering to said human a dietary supplement according to any of claims 1–4, wherein said dietary supplement is administered prior to consumption of high-fat food.

8. The method according to claim 7, wherein said dietary supplement is administered 15 minutes prior to consumption of the high-fat food.

9. A method of inhibiting GI tract absorption of dietary lipids comprising administering to a human a dietary supplement according to any of claims 1–4, wherein said dietary supplement is administered prior to consumption of high-fat food.

10. The method according to claim 9, wherein said dietary supplement is administered 15 minutes prior to consumption of the high-fat food.

* * * * *